April 14, 1936. H. COHEN Re. 19,924

TOURNIQUET

Original Filed Nov. 12, 1931

INVENTOR
Harry Cohen
BY
Austin & Dix
ATTORNEYS

Reissued Apr. 14, 1936

Re. 19,924

UNITED STATES PATENT OFFICE 19,924

TOURNIQUET

Harry Cohen, New York, N. Y., assignor to Milbert Company

Original No. 1,953,074, dated April 3, 1934, Serial No. 574,636, November 12, 1931. Application for reissue June 27, 1935, Serial No. 28,780

7 Claims. (Cl. 128—327)

This invention relates to tourniquets.

The main object of the invention is to provide a device of this kind which is very simple, easily applied to the limb of the patent and extremely effective.

Another object of the invention is to provide a device of this kind which will partially constrict a limb of a patient so as to make the veins below stand out prominently for making a medical test.

Another object of the invention is to provide a device of this kind having means to regulate the pressure of the gripping members exerted on the limb.

Another object of this invention is to construct the gripping members so that they will not cut or pinch the flesh of the patient.

Still a further object of the invention is to provide a ratchet mechanism for holding the gripping members in the desired locked position.

Other objects will appear as the disclosure progresses. The drawing is intended to merely indicate a possible embodiment of the invention. It is obvious that the actual needs of manufacture may necessitate certain mechanical changes. It is therefore not intended to limit the invention to the embodiment illustrated but rather to define such limits in the appended claims.

For a more general understanding of the invention attention is called to the drawing. In the drawing like reference characters denote like parts throughout the specification.

Figure 1:
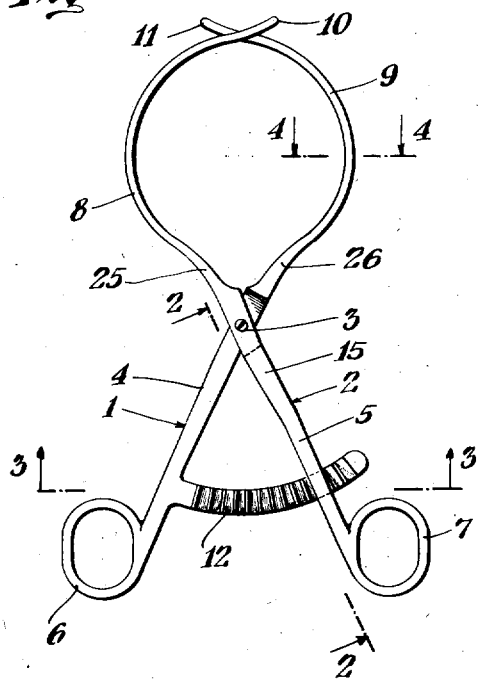
Fig. 1 is a front view of the tourniquet.
Figure 2:
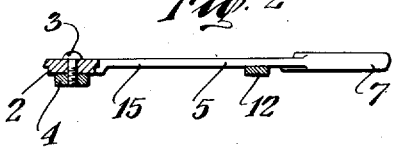
Fig. 2 is a section substantially on line 2—2 of Fig. 1.

Referring now to the drawing in detail, numerals 1 and 2 designate a set of complementary members hinged together by the screw 3.

Each of said members comprises a handle portion 4 and 5 terminating at the bottom into eyes 6 and 7 for the insertion of the fingers of the operator and at the upper ends into curved gripping members 8 and 9 adapted to fit the limb of the patient.

It will be noted by referring to Fig. 1 that the inside curvature of the tip portions 10 and 11 and the butt portions 25 and 26 of the gripping members extend in a reverse direction to the curvature of the intermediate sections thereof. The tip portions and the butt portions are accordingly spaced away from the limb at these points when the clamp is applied so as not to pinch the flesh or skin of the patient.

Figure 3:
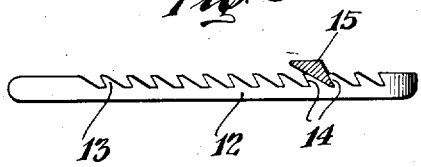
Fig. 3 is an enlarged section substantially on line 3—3 of Fig. 1.
Figure 4:
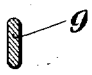
Fig. 4 is a section on line 4—4 of Fig. 1.

Attached to the handle 4 is an arc-like ratchet 12 adapted to cooperate with the handle 5 for the purpose of locking the instrument around the limb of the patient. As noted in Fig. 3 the ratchet is provided with a series of saw teeth which engage with the handle 5. The perpendicular portion 14 of the teeth as noted in Fig. 3 are somewhat inclined so that the handle member will lock in place and thus avoid any accidental separation. The portion 15 of the handle 5 is somewhat thin so as to make the same resilient at that particular place. Normally the handle is tensioned against the ratchet so that it will lock itself in with the ratchet teeth 13. Now when the said handle member is moved the resilient or thinned portion 15 will allow same to easily bend and clear the teeth, thus making the instrument easily operable. The gripping members 8 and 9, as shown in Fig. 3, are preferably wide and somewhat flexible so as not to pinch the tissues or cut the flesh. If desired, they can be covered up with rubber hose to give to the said members a pliable effect.

Figure 5:
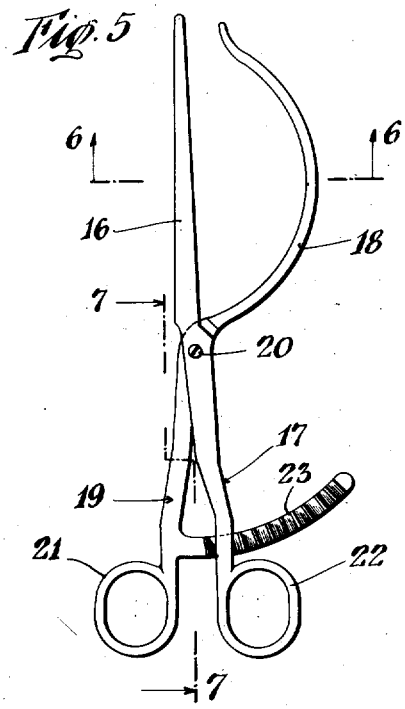
Fig. 5 is a front view of a modified form of the invention.
Figure 6:
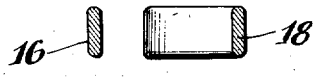
Fig. 6 is a section on line 6—6 of Fig. 5.
Figure 7:
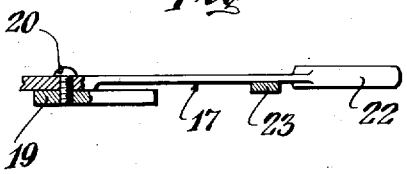
Fig. 7 is a section substantially on line 7—7 of Fig. 5.

The modified form of the invention shown in Fig. 5 is the same as that shown in Fig. 1 with the exception that the gripping member 16 leading from the complementary member 17 is made straight while the gripping member 18 leading from the complementary member 19 is curved similar to the member 9. Numeral 20 designates the pivoting screw connecting the two complementary members 17 and 19 together, 21 and 22 the eyes and 23 the arc-shaped ratchet for regulating the opening of the gripping members and keeping them in a set position. This form of the invention is mainly adapted for operating on patients when lying in bed. The straight gripping member 16 can easily be pushed underneath the patient's arm or leg without disturbing and without the necessity of raising his limb.

It will thus be seen that I have provided a simple and efficient tourniquet which is easy to operate and which will not annoy or disturb the patient. The device can be manipulated with the fingers of one hand only and locks itself up automatically in place. By moving the two eyes together the two gripping members will simultaneously move together and vice versa, when the eyes are separated the gripping members will move away from each other.

Having described my invention, I claim:

1. In a device of the class described, the combination of two complementary members pivotally fastened together, gripping members formed at the upper part of said complementary members, one of said gripping members being straight and the other of said members being curved outwardly, handles at the lower ends of said complementary members, and means to fasten said handles together in a variety of positions.

2. In a device of the class described, the combination of two complementary members pivotally fastened together in the center, gripping members formed at the upper part of said complementary members, one of said gripping members being straight and the other of said members being curved outwardly, the tip of said curved member bent in the reverse direction to the curvature of said curved member, the point of said straight member extending beyond the said tip of the curved member, an arc-shaped ratchet attached to one of said handles and adapted to engage with the other of said handles.

3. In a device of the kind described the combination of two complementary members pivotally fastened together substantially in the center, operating handles at the lower ends of said complementary members, curved gripping members at the upper part of said complementary members, the tips of said curved gripping members bent in a reversed direction to the curvature of said curved gripping members and overlapping each other when the said curved gripping members are brought together to embrace a limb, and means to lock said curved gripping members together in a variety of positions, said means including a ratchet attached to one of the handles and adapted to engage with the other handle, a portion of the said last mentioned handle which engages with the said ratchet being thinned.

4. In a device of the class described, the combination of two complementary members pivotally fastened together, gripping members formed at the upper part of said complementary members, one of said gripping members being straight and the other of said members being curved outwardly, handles at the lower ends of said complementary members, means to fasten said handles together in a variety of positions, said means including a ratchet attached to one of the handles and adapted to engage the other one of said handles.

5. In a device of the class described, the combination of two complementary members pivotally fastened together, gripping members formed at the upper part of said complementary members, one of said gripping members being straight and the other of said members being curved outwardly, handles at the lower ends of said complementary members, means to fasten said handles together in a variety of positions, said means including a ratchet attached to one of the handles and adapted to engage the other one of said handles, a portion of the last mentioned handle which engages with said ratchet being thinned.

6. A physician's and surgeon's clamp tourniquet including complementary members hinged together, said members comprising curved limb gripping portions, and handle portions for manipulating said gripping portions, the inside curvature of the tip and butt ends of said curved gripping portions extending in a reverse direction to the curvature of the intermediate portions thereof so that said gripping elements will not pinch or bind the flesh of the patient when the clamp is applied, and quick release means for automatically retaining said gripping portions in the position to which they have been adjusted by said handle manipulating means.

7. A physician's and surgeon's clamp tourniquet including, complementary members hinged together, said members comprising curved limb gripping portions, and handle portions for manipulating said gripping portions, the inside curvature of the tip and butt ends of said curved gripping portions extending in a reverse direction to the curvature of the intermediate portions thereof so that said gripping elements will not pinch or bind the flesh of the patient when the clamp is applied, said gripping portions having substantially flat limb-engaging faces which comfortably compress the limb of the patient when applied without cutting or welting the flesh, and releasable means for retaining said gripping portions in the position to which they have been adjusted by said handle manipulating means.

HARRY COHEN.